(12) United States Patent
Painchaud et al.

(10) Patent No.: US 8,794,490 B2
(45) Date of Patent: Aug. 5, 2014

(54) LIQUID DISPENSING DEVICE EQUIPPED WITH A SEALING COMPONENT MOVEABLE UNDER THE EFFECT OF PRESSURE BY A USER

(75) Inventors: Gaetan Painchaud, Francheville (FR); Guillaume Grevin, l'Isle d'Abeau (FR); Xavier Julia, Villefontaine (FR); Sylvain Lanzi, Chirens (FR)

(73) Assignee: Rexam Healthcare la Verpilliere (FR)

( * ) Notice: Subject to any disclaimer, the term of this patent is extended or adjusted under 35 U.S.C. 154(b) by 982 days.

(21) Appl. No.: 12/579,750

(22) Filed: Oct. 15, 2009

(65) Prior Publication Data

US 2010/0096416 A1   Apr. 22, 2010

(30) Foreign Application Priority Data

Oct. 15, 2008   (FR) ...................... 08 05715

(51) Int. Cl.
*B65D 47/28* (2006.01)
(52) U.S. Cl.
USPC ............ 222/496; 222/493; 222/514; 222/521
(58) Field of Classification Search
USPC ......... 222/492–496, 521, 525, 491, 499, 513, 222/514, 520
See application file for complete search history.

(56) References Cited

U.S. PATENT DOCUMENTS

| | | | | |
|---|---|---|---|---|
| 1,621,097 A * | 3/1927 | Zammataro | .................... | 222/496 |
| 1,911,616 A * | 5/1933 | Gruber | ......................... | 222/492 |
| 2,628,004 A * | 2/1953 | Schlicksupp | .................. | 222/493 |
| 2,711,271 A * | 6/1955 | Schlicksupp | .................. | 222/493 |
| 3,076,583 A * | 2/1963 | Eberspacher | .................. | 222/493 |
| 4,506,809 A * | 3/1985 | Corsette | .......................... | 222/213 |
| 5,004,127 A * | 4/1991 | Morel | ............................ | 222/521 |
| 5,033,647 A * | 7/1991 | Smith et al. | ..................... | 222/94 |
| 5,154,325 A * | 10/1992 | Ryder et al. | ............. | 222/189.06 |
| 5,226,568 A * | 7/1993 | Newton et al. | ................. | 222/212 |
| 5,431,310 A | 7/1995 | Kanner et al. | | |
| 5,971,232 A * | 10/1999 | Rohr et al. | ..................... | 222/494 |
| 6,202,901 B1 * | 3/2001 | Gerber et al. | .................. | 222/494 |
| 6,273,305 B1 * | 8/2001 | Fioravanti et al. | ............ | 222/494 |
| 6,386,395 B1 * | 5/2002 | Lunghetti | ...................... | 222/213 |
| 6,662,977 B2 * | 12/2003 | Gerber et al. | .................. | 222/494 |
| 6,974,053 B2 * | 12/2005 | Lautre et al. | .................... | 222/92 |
| 2003/0094467 A1 * | 5/2003 | Dark | ............................. | 222/484 |

(Continued)

FOREIGN PATENT DOCUMENTS

DE   19510007 A1   10/1995
EP   0624526 A2   11/1994

(Continued)

OTHER PUBLICATIONS

English translation of FR 2838108, published Oct. 10, 2003.*

(Continued)

*Primary Examiner* — Kevin P Shaver
*Assistant Examiner* — Robert Nichols, II
(74) *Attorney, Agent, or Firm* — St. Onge Steward Johnston & Reens LLC

(57) ABSTRACT

A liquid dispensing device including a sealing component which can take up a liquid release position and a liquid blocking position. The liquid dispensing device also includes a surface for immobilising the sealing component in its blocking position, configured to prevent the sealing component from taking up its liquid release position.

8 Claims, 3 Drawing Sheets

(56) References Cited

U.S. PATENT DOCUMENTS

| | | | |
|---|---|---|---|
| 2004/0112920 A1* | 6/2004 | Felten et al. | 222/212 |
| 2006/0197042 A1* | 9/2006 | Kneer | 251/82 |
| 2006/0249545 A1* | 11/2006 | Ramsey | 222/494 |
| 2007/0045356 A1* | 3/2007 | Foster et al. | 222/494 |
| 2008/0067194 A1 | 3/2008 | Faurie | |

FOREIGN PATENT DOCUMENTS

| | | | |
|---|---|---|---|
| FR | 2395682 | A7 | 1/1979 |
| FR | 2838108 | A1 | 10/2003 |
| FR | 2782137 | A1 | 12/2005 |
| GB | 1593084 | A | 7/1981 |
| JP | S57154663 | A | 9/1982 |
| JP | H03240656 | A | 10/1991 |
| JP | 2005335752 | A | 12/2005 |
| JP | 2006232327 | A | 9/2006 |
| WO | 8601489 | A1 | 3/1986 |
| WO | 9964313 | A1 | 12/1999 |
| WO | 2004011345 | A1 | 5/2004 |

OTHER PUBLICATIONS

International Search Report; FR 0805715; May 6, 2009; 2 pages.
Notice of Reasons for Rejections Application No. 2009-238607 Mailing Date: Oct. 1, 2013 6 pages.

* cited by examiner

LIQUID DISPENSING DEVICE EQUIPPED WITH A SEALING COMPONENT MOVEABLE UNDER THE EFFECT OF PRESSURE BY A USER

CROSS-REFERENCE TO RELATED APPLICATIONS

The present application claims priority of French patent application No. 0805715 filed on Oct. 15, 2008, the content of which is incorporated herein by reference.

FIELD OF THE INVENTION

This invention relates to the technical field of liquid dispensing. In particular, but not exclusively, it concerns the field of dispensing liquid in drop form, such as ophthalmic liquid.

BACKGROUND OF THE INVENTION

Devices implementing this type of dispensing are already known in the state of the art. According to an example described in document FR 2 872 137, the liquid dispensing orifice can be sealed using a cap equipped with a needle entering the dispensing head nozzle and a skirt covering this nozzle. This type of cap prevents liquid escaping from the device when it is not being used.

This invention seeks in particular to provide a device offering better sealing of the dispensing nozzle when the device is not used, in particular during transport or storage of the device.

SUMMARY OF THE INVENTION

The invention therefore relates to a liquid dispensing device comprising a sealing component which can take up a liquid release position and a liquid blocking position, the device also comprising means for immobilising the sealing component in its blocking position, configured to prevent the sealing component from taking up its liquid release position.

The invention therefore ensures that the device provides good sealing if this device includes this type of sealing component. This component providing the sealing may also be called a "sealing valve". It generally comprises a sufficiently flexible elastomer or thermoplastic material and is intended to allow liquid to flow in one direction only, for example when the user exerts a pressure on the reservoir. Note that it is possible to switch from the liquid release position to the liquid blocking or non-return position by moving the component and/or by elastic deformation of all or part of the component.

Immobilising the sealing component in its liquid blocking position guarantees that the sealing component will not accidentally move to its release position, which is especially advantageous during storage, transport or other handling operations of the device before use, for example by a child. For a device equipped with a movable sealing component, therefore, it may be useful to briefly immobilise the component, using temporary immobilisation means, these means being for example detachable or fusible, the fusible means being broken the first time the device is used.

Apart from the fact that liquid cannot escape from the device, the device is also "cleaner". During storage, if the component is not immobilised, liquid could accidentally flow between the sealing component and a cap of the device and stagnate in this volume. Presence of liquid outside the sealed area (enclosed in particular by the reservoir and the sealing component) is dangerous since the liquid could become contaminated.

A device according to the invention may also comprise one or more of the following characteristics.

The immobilisation means exert a pressure on the sealing component, so as to prevent it from moving to its liquid release position. This pressure may be direct or indirect.

The device comprises an outer envelope covering in particular the sealing component, this envelope comprising a liquid release orifice, the sealing component comprising a distal end projecting from the liquid release orifice. Thus, as the distal end of the sealing component is not in setback relative to the surface of the liquid release orifice, it is more easy to isolate the drops from the surface of the outer envelope.

The device also comprises means for pressing on the sealing component, for example arranged on an inner core of the nozzle, exerting on this component a pressure opposite to the pressure exerted by the immobilisation means. Thus, when the immobilisation means are activated on the device, this pressure in opposite directions prevents the sealing component from moving in the dispensing device. In other words, the sealing component is jammed by pinching between the immobilisation means and the pressing means.

The device comprises a removable cap and the immobilisation means are activated when the cap is fitted on the device. Consequently, fitting the cap on the device immobilises the sealing component. This type of immobilisation is easy to implement, the cap generally being fitted on the device if there is a risk of accidentally releasing liquid, especially during transport or storage, before the device is commercialised or in the home.

The immobilisation means are supported by the cap.

The immobilisation means supported by the cap comprise a surface pressing on the sealing component. According to one example, this pressing surface is supported by a projection, projecting out from an inner surface of the cap, designed to press on the sealing component. This projection may take different shapes: it may comprise an annular rib formed on the inner surface of the cap, this annular rib possibly being divided into sectors separated by spaces, or the projection may comprise a pin going inside the nozzle, in a liquid flow channel, and pressing on the sealing component. According to another example, the pressing surface is not projecting and is formed on the inner surface of the cap. According to a further example, the pressing surface corresponds to the bottom of a recess arranged inside the cap. The pressing surface is arranged opposite or staggered with respect to the pressing means described above, formed in an inner core, and exerting a force opposite to that of these pressing means. Sealing is therefore provided by compression and/or deformation of the sealing component.

The device comprises venting means allowing air to enter into a reservoir. The venting of the reservoir, also called entering of air into the reservoir, permits to compensate a depression generated by the pressing of a user to deliver the liquid. Thus the reservoir can take back its original form after the dispensing of liquid.

The cap comprises, in addition to the immobilisation means for the sealing component, means for an airtight sealing of the device, preventing air from passing through the venting means when the cap is fitted on the device. This embodiment is particularly advantageous. It is thus possible to prevent liquid from evaporating during the storage of the device, or else the contamination of the liquid by components existing in the air.

The airtight sealing means comprise an annular rib projecting inside from a wall of the cap and being clamped against a wall for ensuring the airtight sealing.

The device comprises an outer envelope covering in particular and at least partially the sealing component, this envelope comprising a liquid release orifice, and the pressing surface of the immobilisation means being arranged opposite or inside this orifice when the cap is fitted on the device.

The outer envelope comprises an inner opened projection intended to encircle the distal end of the sealing component. This inner projection thus ensures a guiding of the distal end of the sealing component. In particular, it prevents the sealing component from changing its axle relative to its support during the movement into the liquid release or blocking position.

The inner opened projection is formed by an annular rib ending by the liquid release orifice. This annular rib can thus encircle the distal end of the sealing component to ensure its guiding.

The outer envelope comprises a bearing seat for a return element holding the sealing component in blocking position, the seat being arranged around the inner opened projection.

The sealing component is configured to take up its liquid release position under the effect of pressure created by a user action and the immobilisation means prevent the sealing component from taking up its liquid release position under the effect of such pressure created by a user action.

BRIEF DESCRIPTION OF THE DRAWINGS

The invention will be better understood from the following description, given solely by way of example and by referring to the drawings wherein.

DETAILED DESCRIPTION OF THE INVENTION

Figure 1:
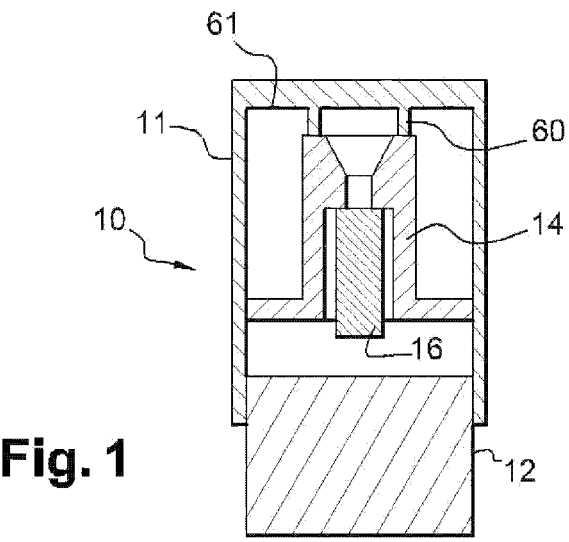
FIG. 1 is a diagrammatic view functionally illustrating a device according to one embodiment of the invention.

A liquid dispensing device comprises a nozzle 10, represented partially and schematically on FIG. 1, designed to be attached to a reservoir made of either plastic, glass or metal, containing the liquid to be dispensed. The device can be used to dispense predetermined liquid doses, more precisely drops of liquid or a spray. The liquid is intended for ocular, nasal or oral application. For example, the device dispenses collyrium drops for the eyes. The nozzle 10 is fitted on a reservoir 12, more precisely on the neck 12 of the reservoir. In this example, the reservoir is made of plastic and is intended to be pressed by the user to make the liquid come out. Other types of reservoir could also be considered, the user being able to release liquid by an action other than pressing it, for example by pressing on a pump activation element.

The nozzle 10 comprises a sealing component 14, arranged between a first part (e.g., an inner core 16) and a second part (e.g., an outer envelope 18) of the nozzle 10. This sealing component 14, or sealing valve, may take up a liquid blocking or non-return position, illustrated on FIGS. 1, 2 and 3, preventing liquid from returning once it has left the sealed zone, and a liquid release position (not shown). Preferably, component 14 is arranged near the distal end of the nozzle 10, near a liquid release orifice 64 (see FIG. 3). More precisely, in the example described, the distal end of the component 14, the end through which the liquid comes out, projects out slightly from the orifice 64. As a variant, this end could be flush with the surface of the orifice 64, or be set back inside the nozzle 10. The end of the component 14 could also project more from the surface of the outer envelope 18, in order to isolate the drops more easily with respect to the surface of the envelope.

In addition, the nozzle 10 is covered by a closure cap 11, detachably mounted on the device so as to protect the device when it is not used. The cap is for example screwed onto the neck of the reservoir 12.

The cap 11 supports means 60 for immobilising the sealing component 14 in its blocking position, configured to prevent the sealing component from moving to its liquid release position, especially under the effect of a pressure exerted on the reservoir 12. The immobilisation means 60 are activated when the cap 11 is mounted on the device. In this example, they comprise a pressing surface, supported by a projection 60, designed to press on the sealing component 14, more precisely an annular rib 60 formed on the inner surface 61 of the cap 11, opposite the liquid release orifice 64 of the nozzle 10.

The configuration of the nozzle 10 according to a special embodiment will be described more precisely, in reference to FIGS. 2 and 3. The example of FIG. 3 corresponds to a slight variant of the example of FIG. 2. On FIG. 2, the sealing component 14 consists of two parts 34, 36 and is held in blocking position by a return element 15, whereas on FIG. 3, component 14 is made completely from elastomer material and is kept in blocking position by deformation, as described below.

Figure 2:
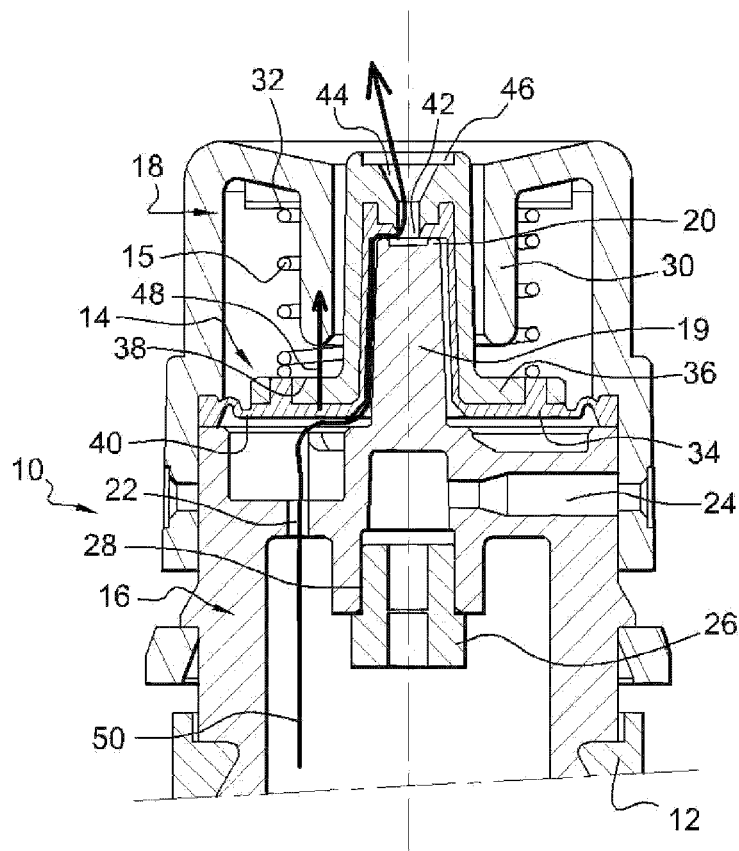
FIG. 2 is a longitudinal sectional view illustrating an example of device as schematised on FIG. 1.

As shown on FIG. 2, the first part 16 of the nozzle 10 is an inner core 16, comprising a substantially cylindrical protuberance 19 projecting from the distal end of the core 16. On its distal end, this protuberance 19 supports means 20 for pressing on the sealing component 14, these means 20 being in this example composed of a projection forming an annular flange designed to press on the sealing component 14. As an alternative, the pressing means 20 could consist only of the end of the protuberance 19, without including a projection on this end. The inner core 16 also comprises a channel 22 for the liquid to flow from the reservoir to the outside of the device, as well as a part connecting the core 16 to the reservoir 12. The nozzle 10 also comprises venting means, designed to allow air to enter the reservoir to make up for the depression generated by the pressure exerted by the user to make liquid come out. In this example, the venting means are supported by the inner core 16 and comprise an air channel 24, crossed by a hydrophobic filter 26, designed to filter the incoming air without, however, allowing liquid to escape via the channel 24. More precisely in this example, the filter 26 is arranged in a filter housing 28, this housing 28 consisting of an annular rib arranged in the centre of the inner surface of the core 16, in which the filter 26 is fitted.

The second part of the nozzle 10 corresponds, in this example, to an outer upper envelope 18 of the nozzle 10. This outer envelope 18 is designed to cover the inner core 16, the sealing component 14 and the spring 15. More precisely, it comprises an open inner protuberance 30 formed by a central annular rib opening onto the orifice 64, designed to surround the distal end of the protuberance 19 and the sealing component 14 allowing liquid to come out of the device. The envelope 18 also comprises a seat 32 to support the return element 15, this seat 32 being arranged around the protuberance 30.

In this example, the sealing component comprises an elastomer part 34 and a rigid part 36, parts 34 and 36 being fastened to each other in displacement, which means that when part 34 is displaced, part 36 is displaced with it, and vice versa. In this example, parts 34 and 36 are assembled by overmoulding, but other types of assembly could be considered. The elastomer part 34 is made from an elastomer material such as silicone or an elastomer thermoplastic material. The rigid part 36 is made from a plastic material such as polypropylene. The rigid part 36 comprises a surface 38 to support the return element 15. As can be seen on the figures, the rigid part 36 covers the elastomer part 34 over substantially its entire surface, a zone 40 of the elastomer part nevertheless being left free at the end of the elastomer part, to allow this elastomer part 34 to extend. More precisely, the elastomer part 34, and the rigid part 36, each have the shape of a hat with a central cylindrical shape, of shape substantially complementary to that of the protuberance 19 of the core 16, this cylindrical shape being extended on its proximal end by an edge. The rigid part 36 therefore covers the elastomer part 34 over a large proportion of its surface, except around its periphery 40. As can be seen on the figures, parts 34, 36 define a channel 42, arranged on the bottom of their central cylindrical shape, allowing the liquid to come out. Moreover, the rigid part 36 comprises means 44 for forming liquid drops. More precisely, these means 44 have the shape of a cone starting from the channel 42 and widening towards the distal end of the device, so as to form a drop and avoid the liquid being dispensed in a jet, cone 44 leading out onto a cylindrical portion 46, used to calibrate the drop.

In this example, the return element 15 is a helical metallic spring. This element 15 exerts a return force on the sealing component 14, by pressing on the surface 38 of the rigid part 36, so as to return the sealing component 14 to its liquid blocking position.

As can be seen on the figures, the sealing component 14 is sealed (static sealing) between the two parts 16, 18, so that liquid flowing through the channel 22 does not escape inside the envelope 18.

The operation of the dispensing device shown on FIG. 2 will now be described.

When the cap 11 is mounted on the device, the immobilisation means 60 are activated and the component 14 is therefore immobilised. More precisely, the pressing means 20 exert on the component 14 a pressure opposite to the pressure exerted by the immobilisation means 60. Consequently, the component 14 is compressed against the core 16, thereby sealing the assembly.

To use the device, the cap 11 is first removed, which deactivates the immobilisation means 60, thereby allowing the component 14 to move between its two positions. To dispense liquid drops, the user presses the device reservoir, making liquid flow into the channel 22 and therefore exerting a pressure on the elastomer part 34. Under the effect of this pressure, the sealing component moves from its liquid blocking position to its liquid release position, making a translation upwards, as shown by the arrow 48. More precisely, the zone 40 of the elastomer part 34 deforms, by extending, to allow this upward displacement of the elastomer part. After this displacement, the seal provided by cooperation of the pressing means 20 with the sealing component 14 is broken, and liquid can flow through the channel 42 up to parts 44, 46, to form a liquid drop. The liquid path is illustrated by the arrow 50. Once the drop has been released, the user no longer needs to press on the reservoir which fills with air through channel 24. In addition, since the pressure of the liquid coming out has stopped, the sealing component 14 returns to its liquid blocking position under the effect of the return force provided by element 15. The pressing means 20 and the elastomer part of the component 14 therefore cooperate again to prevent liquid from coming out.

By replacing the cap on the nozzle, the component 14 can be immobilised in this position again, preventing the contamination of any liquid which has accidentally escaped outside the sealed zone.

The advantages of the dispensing device of this example include in particular the fact that the rigid part 36 forms a kind of shell for the elastomer part 34, making it easier to exert stress on the sealing component 14 without risk of deforming it.

Note that variants of the example described are possible. In particular, the return element 15 is a helical spring, but other types of return element could be considered, made from metal or not, such as a rubber strip or an elastomer element. In particular, this return element 15 could be integrated directly in the sealing component 14, being integrated either in its elastomer part 34 or in the rigid part 36, or be directly integrated in part 18.

Figure 3:
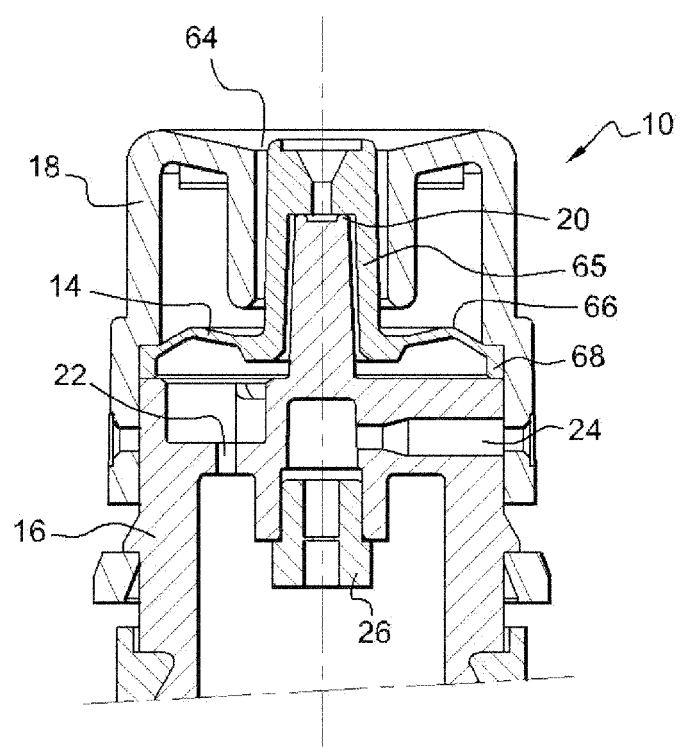
FIG. 3 is a view similar to FIG. 2, illustrating a variant of the example of FIG. 2.

On the variant of FIG. 3, the sealing component is made fully from an elastomer material and the nozzle does not have a spring. In this example, the component 14 is mounted deformed on the device to block the liquid. The component 14 is in fact hat-shaped, with a cylindrical shape 65 and an edge 66. The periphery 68 of this edge is attached permanently between parts 16 and 18, so as to provide static sealing. This attachment is made by deforming the component 14: it is fitted on the protuberance 19 and deformed such that the component 14 is forced to press against the protuberance 19, more precisely against the means 20. The shape of the component 14 illustrated on FIG. 3 is in fact different from that of the component 14 before assembly. Pressing the component 14 guarantees sealing in the blocking position.

Operation of the device of FIG. 3 is similar to that of FIG. 2.

Figure 4:
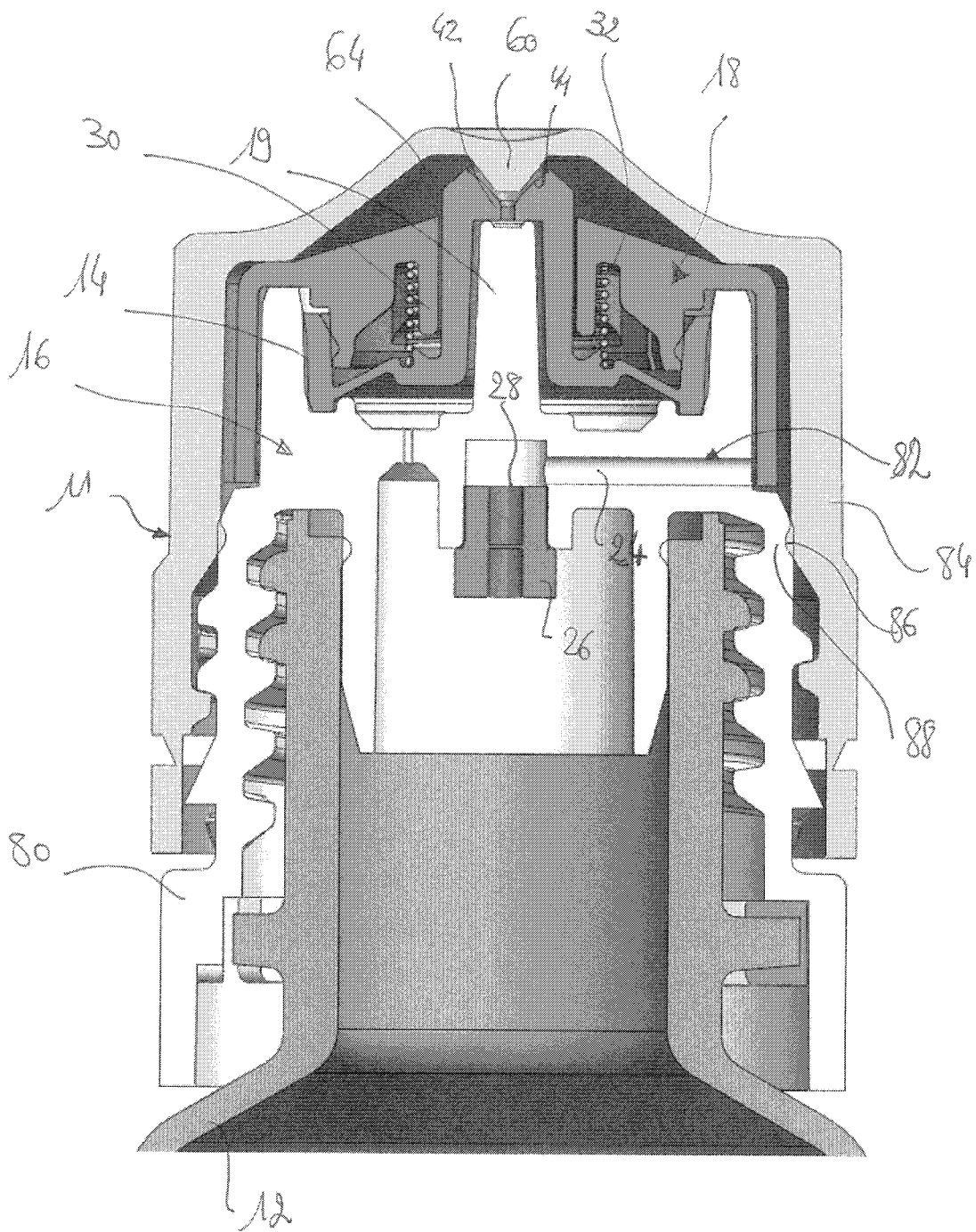
FIG. 4 is a view similar to FIG. 2, illustrating another variant of the example of FIG. 2, comprising a cap.

On FIG. 4, most of the elements are similar to those of FIGS. 1 to 3. The nozzle 10 is fitted on the neck of the reservoir 12 by screwing a connecting part of the part 16 on the neck, that connecting part comprising here an outer wall 80 screwed on the neck. Similarly to other figures, the part 16 also comprises venting means 82, allowing air to enter into the reservoir to compensate a depression generated by the pressing of the user to dispense liquid. The venting means are supported by the inner core 16 and comprise elements 24, 26, 28. The sealing component is integrally made from an elastomer material, but it could be considered that the sealing component comprises also a rigid part. Furthermore, on FIG. 4, the sealing component 14 projects more than on other figures from the liquid release orifice 64, the distal end 19 of the core 16 being slightly flushed with the opening of the orifice 64 realised in the upper surface of the outer envelope 18. Thus the drops separate even more easily from the upper surface of the envelope 18.

The cap 11 is shown on FIG. 4. In this example, les means 60 for immobilising the sealing component 14 comprise a projection having a sensibly conical form. More precisely, it has a slightly complementary form with the means 44 for forming liquid drops, so that it can better immobilise the distal end of the component 14, by pinching, when the cap 11 is fitted on the device. The cap 11 also comprises a peripheral wall 84 for fixing the cap on the device. The wall 84 is fastened by screwing on the part 16. However, it could be fastened by screwing on the reservoir 12, or also be fastened on one or the other of those elements by snap-fastening. The wall 84 supports means 86 for an airtight sealing of the device, preventing air from passing through the venting means when the cap 11 is fitted on the device. In this example, the means 86 comprise an annular rib projecting inside from the wall 84 of the cap and being clamped against a wall 88 of the part 16 for ensuring the airtight sealing. Indeed, the rib 86 has an inner diameter strictly inferior to the outer diameter of the wall 88, so that, when the cap is screwed on the device, the rib 86 is flattened against the wall 88, preventing air from passing between the parts 86 and 88. The parts 86, 88 define a airtight sealing zone, arranged between the end of the wall 84 of the cap and the venting means 82.

Note that the invention is not limited to the previously described examples. In particular, the shape of the component 14 may vary, as well as the immobilisation method. Amongst the advantages of the device, we see that the cap 11, immobilising the component 14, prevents liquid from entering the unsealed zones of the device, for example between the component 14 and the envelope 18, or the surface of the nozzle 10.

What is claimed is:

1. A liquid dispensing device, comprising:
   a pressing element,
   a sealing component which is moveable with respect to the pressing element between a liquid release position and a liquid blocking position, wherein in the liquid blocking position, the sealing component cooperates with the pressing element,
   an outer envelope, fixed in position with respect to the pressing element, comprising an inner opened projection, extending proximally from the outer envelope, and covering the sealing component, this envelope comprising a liquid release orifice,
   the sealing component comprising a distal end projecting from a liquid release orifice,
   the inner opened projection encircling a part of the distal end of the sealing component so as to ensure a guiding of the distal end of the sealing component during the movement between the liquid release and the blocking position,
   the outer envelope comprising a bearing seat for a return element holding the sealing component in blocking position, the seat being arranged around the inner opened projection,
   the device also comprising a removable cap and an immobilizer retaining the sealing component in its blocking position, configured to prevent the sealing component from taking up its liquid release position, the immobilizer being supported by the cap, exerting a pressure on the sealing component and being activated when the cap is fitted on the device,
   the device also comprising a vent allowing air to enter into a reservoir, and the cap comprising, in addition to the immobilizer for the sealing component, an airtight seal, preventing air from passing through the vent when the cap is fitted on the device.

2. The device according to claim 1, wherein the airtight seal comprises an annular rib projecting inside from a wall of the cap and being clamped against a wall for ensuring the airtight sealing.

3. The device according to claim 1, comprising a protuberance for pressing on the sealing component, exerting on this component a pressure opposite to the pressure exerted by the immobilizer.

4. The device according to claim 3, wherein the immobilizer comprises a pressing surface for pressing on the sealing component, and wherein the pressing surface of the immobilizer is arranged opposite or staggered with respect to the protuberance.

5. The device according to claim 1, wherein the immobilizer comprise a surface for pressing on the sealing component.

6. The device according to claim 5, wherein the surface is a projection designed to press on the sealing component.

7. The device according to claim 5, wherein the surface is an annular rib formed on the inner surface of the cap.

8. The device according to claim 1, wherein the inner opened projection is formed by an annular rib ending by the liquid release orifice.

* * * * *